United States Patent [19]
Watanabe et al.

[11] Patent Number: 5,685,964
[45] Date of Patent: Nov. 11, 1997

[54] OXYGEN CONCENTRATION SENSOR ELEMENT

[75] Inventors: Isao Watanabe; Masahiro Shibata, both of Nagoya; Masaya Fujimoto, Kariya, all of Japan

[73] Assignee: Nippondenso Co., Ltd., Kariya, Japan

[21] Appl. No.: 584,120

[22] Filed: Jan. 11, 1996

[30] Foreign Application Priority Data

Jan. 19, 1995 [JP] Japan .................................. 7-026069

[51] Int. Cl.⁶ .................................................. G01N 27/26
[52] U.S. Cl. .......................................... 204/429; 204/425
[58] Field of Search ................................. 204/421, 424, 204/425, 426, 427, 429

[56] References Cited

U.S. PATENT DOCUMENTS

| | | | |
|---|---|---|---|
| 4,402,820 | 9/1983 | Sano et al. | 204/425 |
| 4,476,008 | 10/1984 | Sano et al. | 204/425 |
| 4,569,748 | 2/1986 | Yamakawa et al. | 204/425 |
| 4,595,485 | 6/1986 | Takahashi et al. | 204/406 |
| 4,716,760 | 1/1988 | Osuga et al. | 204/425 |
| 5,160,598 | 11/1992 | Sawada et al. | 204/429 |
| 5,238,549 | 8/1993 | Makino et al. | 204/425 |
| 5,505,837 | 4/1996 | Friese et al. | 204/429 |

FOREIGN PATENT DOCUMENTS

| | | |
|---|---|---|
| 331513 | 9/1989 | European Pat. Off. . |
| 468500 | 1/1992 | European Pat. Off. . |
| 58-100746 | 6/1983 | Japan . |
| 60-015552 | 1/1985 | Japan . |

*Primary Examiner*—Bruce F. Bell
*Attorney, Agent, or Firm*—Cushman, Darby & Cushman IP Group of Pillsbury Madison & Sutro LLP

[57] ABSTRACT a limiting current type oxygen concentration sensor element includes a measured gas side electrode formed at one side of a solid electrolyte, and a diffusion resistance portion formed on the measured gas side electrode to provide diffusion resistance to passing measured gas therein. The diffusion resistance portion includes a concave portion formed at a position at least corresponding to a position of the measured gas side electrode. In the concave portion, a porous trap layer is disposed to trap contamination in measured gas. The side wall of the concave portion contacts with the trap layer. The area of a contact surface becomes larger than that without the concave portion, which can effectively prevent the trap layer from being peeled off and dropping down. The trap layer can be easily made thicker. By changing the depth of the concave portion appropriately, diffusion resistance of the diffusion resistance portion can be easily adjusted.

19 Claims, 10 Drawing Sheets

OXYGEN CONCENTRATION SENSOR ELEMENT

CROSS REFERENCE OF RELATED APPLICATION

This application is based upon and claims priority from Japanese Patent Application No. 7-26069 filed on Jan. 19, 1995, the content of which is incorporated herein by reference.

BACKGROUND OF THE INVENTION

1. Field of the Invention

The present invention relates to a limiting current type oxygen concentration sensor used for air/fuel ratio control of an automobile engine.

2. Description of Related Art

A conventional limiting current type oxygen concentration sensor is disclosed in Japanese Patent Laid-Open Publication No. 60-15552. In this prior art, a diffusion resistance portion is formed on an electrode of a solid electrolyte at a side for measuring gas and the thickness of the diffusion resistance portion is reduced by cutting or whittling to adjust the diffusion resistance of the diffusion resistance portion.

Although it is not disclosed in the above-mentioned publication specifically, a porous trap layer is generally formed on the diffusion resistance portion to remove poison in the gas to be measured.

However, because the surface of the diffusion resistance portion is cut to be flat as described above, even if the trap layer is formed on the diffusion resistance portion, it is difficult to connect the trap layer with the diffusion resistance portion favorably. Therefore, the trap layer may be peeled off and drop down from the diffusion resistance portion under hard operating condition.

SUMMARY OF THE INVENTION

In light of the above-mentioned problems, an object of the present invention is to provide an oxygen concentration sensor element capable of adjusting diffusion resistance of the diffusion resistance portion and preventing the trap layer formed on the diffusion resistance portion from dropping down.

According to a first aspect of the present invention, a limiting current type oxygen concentration sensor element includes a measured gas side electrode formed at one side of a solid electrolyte, and a diffusion resistance portion formed on the measured gas side electrode to provide diffusion resistance to passing measured gas therein. The diffusion resistance portion includes a concave portion formed at a position at least corresponding to a position of the measured gas side electrode. In the concave portion, a porous trap layer is disposed to trap contamination in measured gas.

It is preferable that the concave portion includes a bottom surface and an inclined wall which inclines toward the bottom surface in such a manner that the bottom surface and said inclined wall forms an acute angle. In this way, the area of the contact surface between the trap layer and the concave portion increases, and the connection of the trap layer with the concave portion becomes stronger by a wedge effect in the concave portion, which can prevent the trap layer from being peeled off and dropping down.

In addition to the concave portion, the trap layer can be provided on the other portion of the diffusion resistance portion, so that the thickness of the trap layer can be thicker compared with the case where a trap layer is formed only on the concave portion. Thus, trap function can be effectively improved.

It is preferable that the trap layer includes a plurality of layers. In such a case, a thicker trap layer can be easily formed.

Porosity of the plural trap layers can be either same or different. When porosity differs, it is preferable that the porosity of the most exterior layer be the highest and the porosity of the most interior layer be the lowest, so that the trap layer will not be clogged and can trap poison more efficiently.

The diffusion resistance portion is a porous layer made of such ceramics as $Al_2O_3$, $MgO.Al_2O_3$ or the like. The above-described diffusion resistance portion may be a pore of approximately 0.1–0.3 mm diameter.

When the solid electrolyte is a flat plate, a reference electrode and a solid electrolyte may be placed on the same plane with a certain distance. The surface of the reference electrode can be covered with a gutter-shaped duct to introduce reference gas, so that the reference electrode can be isolated from measured gas.

According to a second aspect of the present invention, a method for manufacturing a limiting current type oxygen concentration sensor element includes steps of: forming a diffusion resistance portion having diffusion resistance on the measured gas side electrode; forming a concave portion on a surface of the diffusion resistance portion by cutting or whittling with a proper depth; and providing a trap layer for trapping contamination in a measured gas in the concave portion.

Before forming the concave portion by cutting or whittling, the thickness ($L_0$) of the original diffusion resistance portion should be measured first. Then, cut depth ($\Delta L$) of the concave portion is determined by subtracting the thickness ($L_1$) of the needed diffusion resistance portion from the thickness ($L_0$).

As another method, the thickness ($L_0$) of the diffusion resistance portion and a limiting current ($I_0$) in the oxygen concentration sensor element in the original state should be measured in advance, and then the cut depth of the concave portion is determined by the following equation by combining a target limiting current ($I_1$).

$$\Delta L = L_0 - L_1$$
$$= L_0\{1 - (L_1/L_0)\}$$
$$= L_0\{1 - (I_0/I_1)\}$$

In an oxygen concentration sensor element of the present invention, a concave portion is formed on a diffusion resistance portion and a porous trap layer is provided to the concave portion.

The side wall of the concave portion contacts with the trap layer. The area of a contact surface becomes larger than that without the concave portion, which can effectively prevent the trap layer from being peeled off and dropping down. The trap layer can be easily made thicker.

By changing the depth of the concave portion appropriately, diffusion resistance of the diffusion resistance portion can be easily adjusted.

Other objects and features of the invention will appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which.

DETAILED DESCRIPTION OF THE PRESENTLY PREFERRED EXEMPLARY EMBODIMENTS

An oxygen concentration sensor element in an oxygen concentration sensor for automobile exhaust gas according to the preferred embodiments of the present invention is hereinafter described with reference to the accompanying drawings.

A first embodiment of the present invention will be described with reference to FIGS. 1 and 2.

Figure 1:
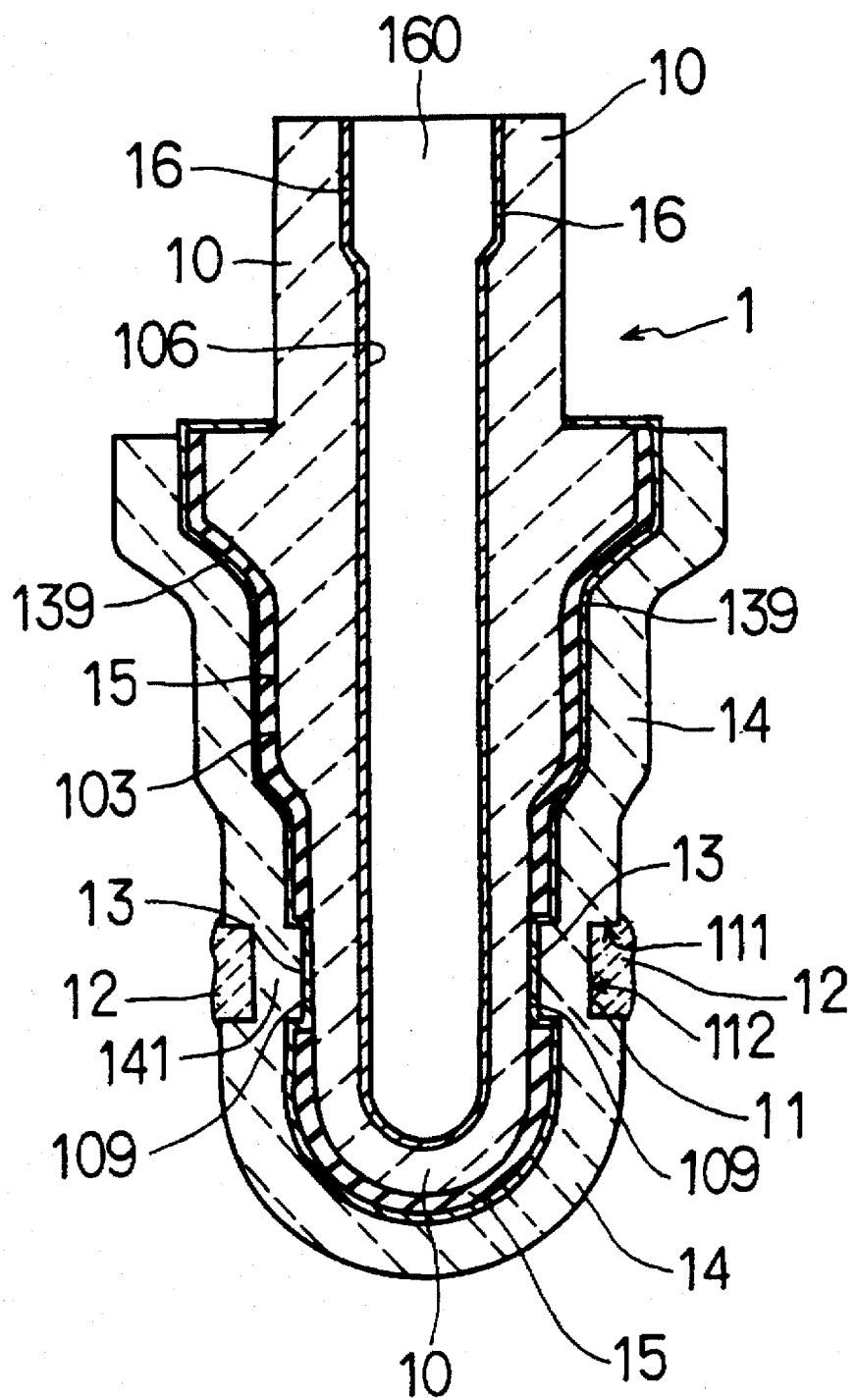
FIG. 1 is a sectional view of an oxygen concentration sensor element according to a first embodiment.

As shown in FIG. 1, an oxygen concentration sensor element 1 of the first embodiment includes a solid electrolyte 10, a reference electrode 16 fixed on an inner surface 106 of solid electrolyte 10, a measured gas side electrode 13 fixed on an outer surface 103 of solid electrolyte 10, and a diffusion resistance portion 14 formed on measured gas side electrode 13. Diffusion resistance portion 14, through which the measured gas passes, has a predetermined resistance against the diffusion of gas, i.e., diffusion resistance.

The above-described diffusion resistance portion 14 has a concave portion 11 at a position at least facing measured gas side electrode 13, and a porous trap layer 12 is disposed in the concave portion 11 to trap contamination in the measured gas. Trap layer 12 contacts with concave portion 11 at a bottom portion 112 and a side wall 111 of concave portion 11.

Diffusion resistance portion 14 is made of a porous layer to introduce measured gas to measured gas side electrode 13. A gas permeability of trap layer 12 is higher than that of diffusion resistance portion 14.

Solid electrolyte 10 is formed in a shape where one end is open and the other end is closed, for example, a cup shape, and includes a reference gas chamber 160 (atmospheric air chamber) therein. An outer surface 103, i.e., the surface other than a belt-like portion 109 surrounding a part of the whole outer surface at the lower end of solid electrolyte 10, is covered with an electrical insulating layer 15.

A platinum layer covers both belt-like portion 109 and electrical insulating layer 15. The platinum layer on belt-like portion 109 serves as measured gas side electrode 13, while the other portion of the platinum layer (a portion other than belt-like portion 109) serves as a lead portion 139 to keep an electrical conductivity with the outside thereof.

Concave portion 11 is disposed to face measured gas side electrode 13.

To manufacture the above-described oxygen concentration sensor element 1, powdered material containing $ZrO_2$, $Y_2O_3$ or the like is prepared, then sintered to produce solid electrolyte 10.

Next, electrical insulating layer 15 is provided on outer surface 103 other than belt-like portion 109 of solid electrolyte 10 by plasma spraying.

A platinum layer is provided on inner surface 106 of solid electrolyte 10, the surface of electrical insulating layer 15, and belt-like portion 109 by chemical plating. The platinum layer on inner surface 106 serves as reference electrode 16. The platinum layer on belt-like portion 109 serves as measured gas side electrode 13, and the platinum layer on electrical insulating layer 15 serves as lead portion 139.

Diffusion resistance portion 14 is provided by plasma-spraying $MgO \cdot Al_2O_3$ on the surfaces of measured gas side electrode 13 and lead portion 139.

Next, concave portion 11 formed in a ring shape is provided by cutting the surface of diffusion resistance portion 14 by a machine tool such as a lathe.

Figure 2:
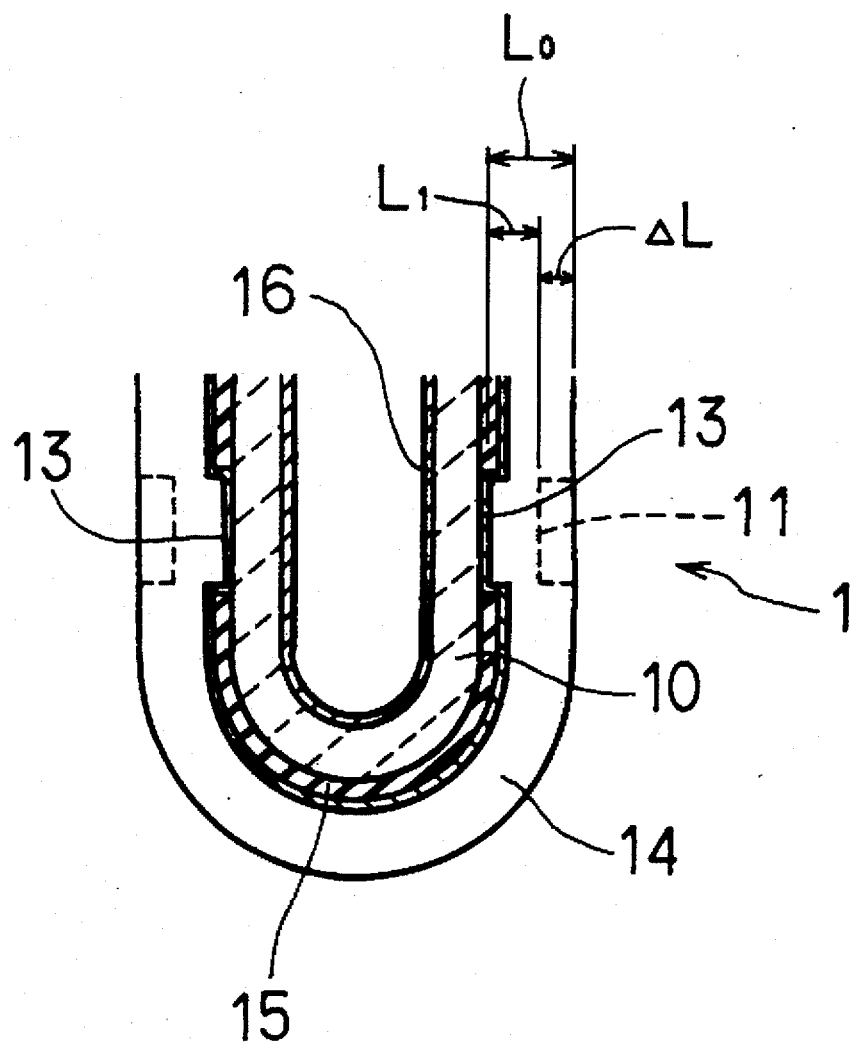
FIG. 2 is an explanatory view of the concave portion of the oxygen concentration sensor element according to the first embodiment.

As shown in FIG. 2, when cutting the surface of diffusion resistance portion 14 to form concave portion 11, the thickness ($L_0$) of the original diffusion resistance portion is measured in advance. Then, depth of concave portion 11 to be cut is determined by subtracting the necessary thickness ($L_1$) of diffusion resistance portion 14 from the above-described thickness ($L_0$). The original thickness ($L_0$) is measured by a non-contact type laser measuring device for measuring an outer diameter As for an example of manufactured size of a belt-like concave portion after trimming the diffusion resistance portion in a cup-shaped element, the width is approximately 7 mm and the depth is approximately 100 μm.

The thickness ($L_0$) of the original diffusion resistance portion is measured by a non-contacting type laser outer diameter measuring device.

First, an outer diameter of each predetermined portion which will be a prospective measured area of solid electrolyte 10 is measured by a laser type outer diameter measuring device before the diffusion resistance layer is formed. Then, diffusion resistance portion 14 will be formed on the surface of solid electrolyte 10.

The outer diameter of solid electrolyte 10 having diffusion resistance portion 14 will be measured similarly by a laser type outer diameter measuring device.

In this way, the thickness of diffusion resistance portion 14 formed on the surface of solid electrolyte 10 can be easily obtained from the relationship between the outer diameter of the solid electrolyte having the diffusion resistance portion and the diameter of the solid electrolyte without the diffusion resistance portion.

In this embodiment, non-contact type laser outer diameter measuring device is used, however, any other measuring methods can be employed. A contact type measuring device, for instance, slide calipers can be also used for the present invention.

Finally, thermally-stable ceramic particles such as α-alumina, mullite, γ-alumina, $MgO.Al_2O_3$ spinel or the like are used to provide trap layer 12 in concave portion 11 by a dipping method, brushing or the like, oxygen concentration sensor element 1 thereby being manufactured.

An operation and an effect of the present embodiment is described.

In oxygen concentration sensor element 1 of this embodiment, concave portion 11 is formed on diffusion resistance portion 14 and trap layer 12 is disposed on the concave portion 11.

Therefore, oxygen concentration sensor element 1 can be freely designed with high discretion. That is, by providing concave portion 11 to the position facing measured gas electrode 13, trap layer 12 can be provided only to the portion where trap layer 12 is exactly needed. Therefore, the amount of material used for trap layer 12 can be minimized.

The contacting area of the element surface of trap layer 12 with diffusion resistance portion 14 becomes larger by side wall 111 of concave portion 11. Therefore, it is effectively prevented that trap layer 12 is peeled off and drops down. Further, it is easy to make trap layer thicker.

Diffusion resistance of the diffusion resistance portion 14 can be easily adjusted by changing the depth of the concave portion 11 as the case may be.

According to oxygen concentration sensor 1 of this embodiment, it is possible to adjust the diffusion resistance of the diffusion resistance portion and further to prevent a trap layer formed on the diffusion resistance portion from dropping down.

Oxygen concentration sensor element 1 of the present embodiment is a limiting current type and solid electrolyte 10 has oxygen ion conductivity. When voltage is applied between the electrodes fixed on the inner and outer surfaces of the element, oxygen molecules in measured gas (exhaust gas) reach measured gas side electrode 13 through trap layer 12 and diffusion resistance portion 14, and are supplied with electrons at measured gas side electrode 13, thereby being oxygen ions. The above-described oxygen ions diffuse and migrate in solid electrolyte 1. The electrons of the ions are released at reference electrode 16 so that the oxygen ions become oxygen molecules.

In the above-described series of reaction, when voltage applied between measured gas side electrode 13 and reference electrode 16 is gradually increased, finally, an electric current will not vary any more. This current is a limiting current and is theoretically obtained by the following formula:

$$I_1 = K \times (S \times B/L_1) \times P$$

Wherein, $I_1$ is a limiting current, K is a constant, S is an area of measured gas side electrode 13, B is a porosity of diffusion resistance portion 14, $L_1$ is thickness of diffusion resistance portion 14, and P is a divided voltage of oxygen in measured gas.

From the above-described formula, it is understood that the limiting current may be influenced by factors including manufacturing errors as the area of measured gas side electrode 13, thickness of diffusion resistance portion 14 and porosity. Further, it is difficult to control the porosity.

In light of the aforementioned problems, a purpose of the first embodiment is to reduce the fluctuation of a limiting current, i.e., an output of oxygen concentration sensor element 1, and to improve durability of measured gas side electrode 13 and diffusion resistance portion 141 covering at least electrode 13 of diffusion resistance portion 14. In short, to achieve the reduction of fluctuation of a limiting current, concave portion 11 is formed on the surface of diffusion resistance portion 14 to adjust the thickness of diffusion resistance portion.

To improve durability of measured gas side electrode 13 and diffusion resistance portion 141 covering at least electrode 13 of diffusion resistance portion 14, trap layer 12 is provided in concave portion 11. In this way, it is easily and certainly possible to provide trap layer 12 on both measured gas side electrode 13 and diffusion resistance portion 141 covering at least electrode 13 to be protected most from poisoning.

Next, a second embodiment of the present invention is described.

Figure 3:
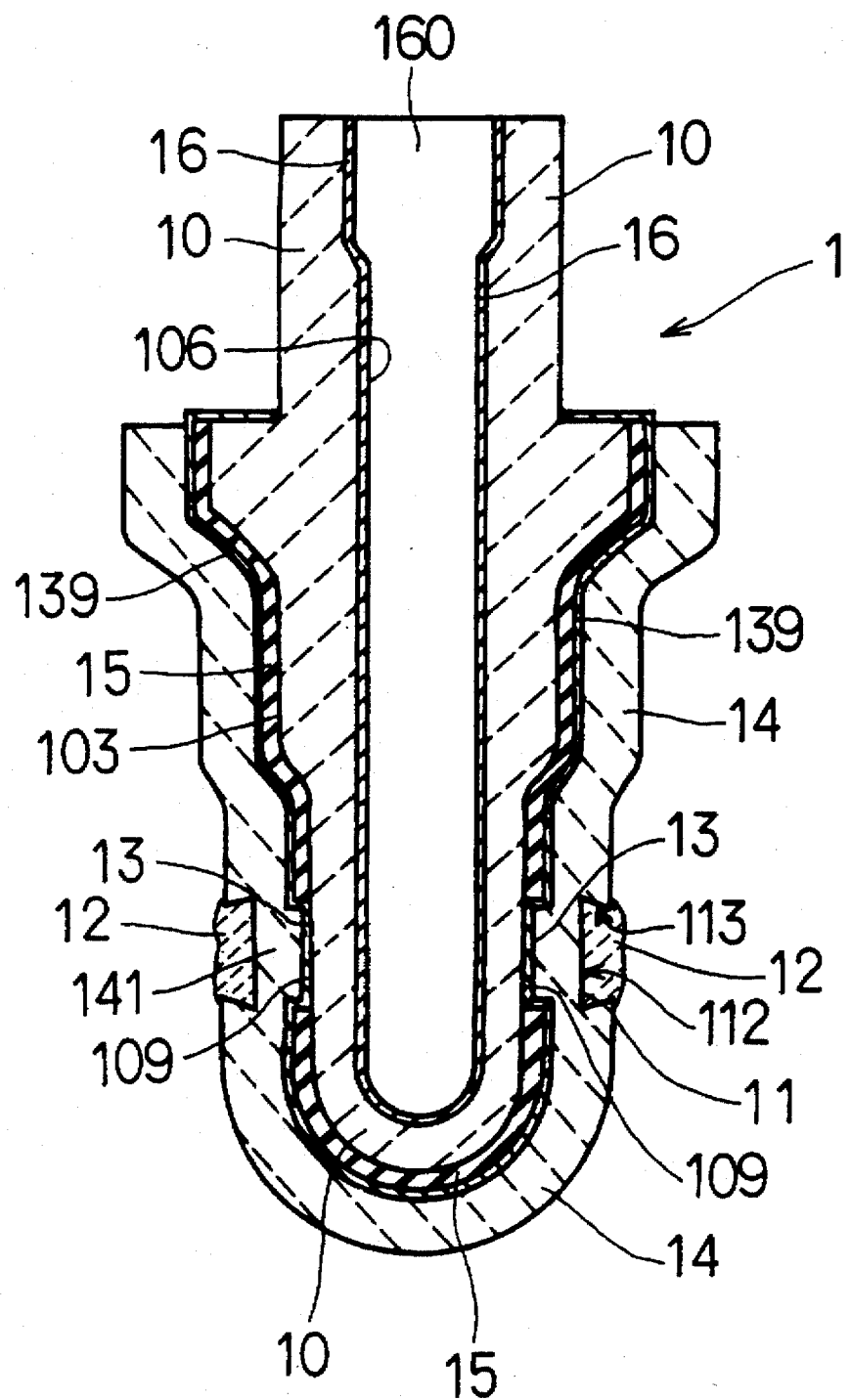
FIG. 3 is a sectional view of an oxygen concentration sensor element according to a second embodiment.

In the second embodiment as shown in FIG. 3, a cross-sectional shape of concave portion 11 of oxygen sensor element 1 in an axial direction is trapezoidal where inclined wall surfaces 113 extend innerwardly to incline toward the bottom surface 112 of concave portion 11.

Concave portion 11 is formed by cutting or whittling the surface of a diffusion resistance portion 14. A trap layer 12 is provided in concave portion 11 to trap contamination in measured gas. Trap layer 12 contacts with bottom surface 112 and inclined wall surfaces 113 of concave portion 11.

Other features are same as in the first embodiment.

Since concave portion 11 has inclined wall surfaces 113 extending toward the bottom of concave portion 11, it can effectively prevent trap layer 12 from being peeled off and dropping down due to a wedge effect in concave portion 11. The second embodiment has the same operation and effect as in the first embodiment.

Next, a third embodiment of the present invention is described.

Figure 4:
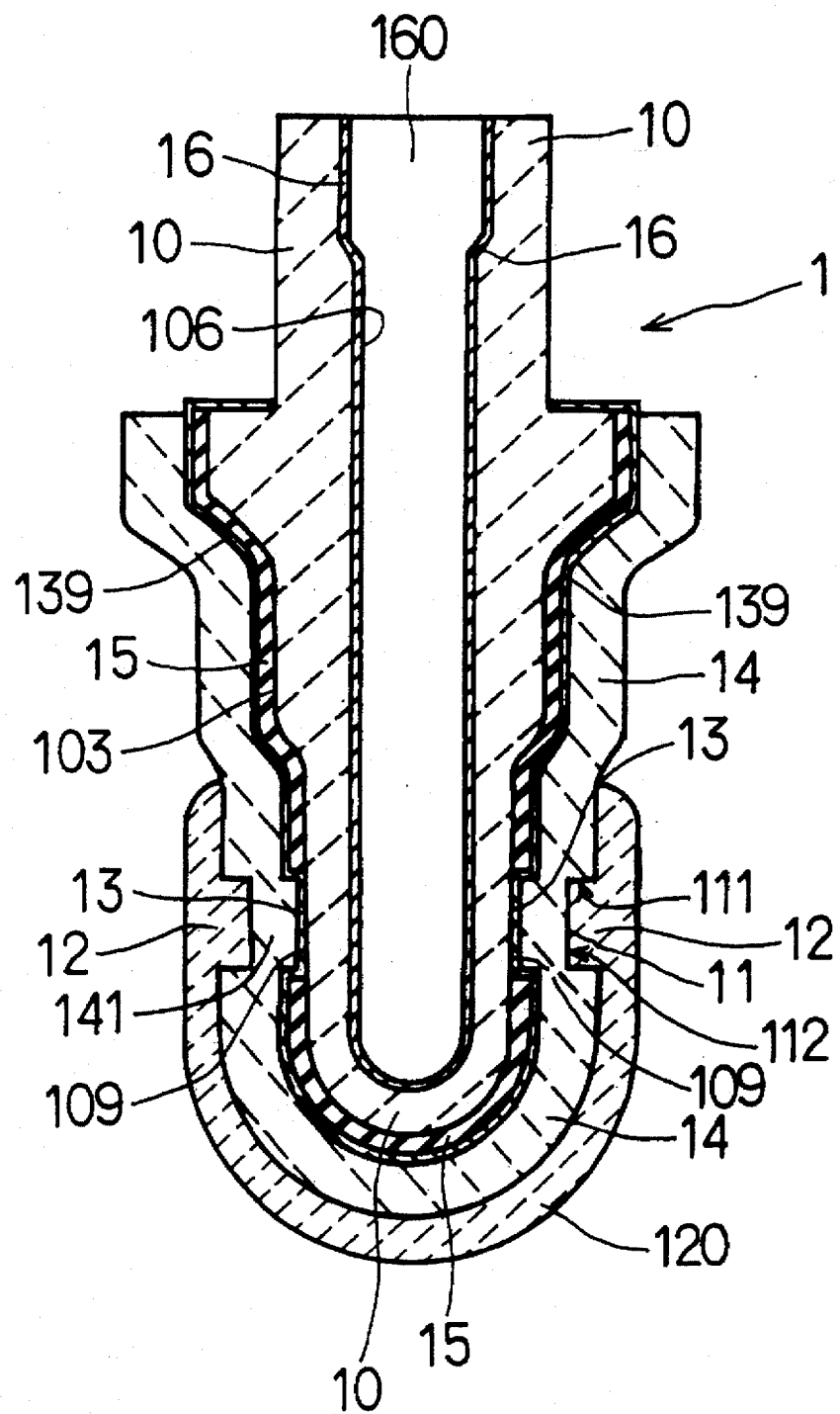
FIG. 4 is a sectional view of an oxygen concentration sensor element according to a third embodiment.

In the third embodiment as shown in FIG. 4, trap layers 12 and 120 are formed on diffusion resistance portion 14 including concave portion 11.

Trap layer 12 is provided to concave portion 11 on diffusion resistance portion 14. Trap layer 120 is formed on the surface of diffusion resistance portion 14 in a manner to entirely cover the lower portion of oxygen concentration sensor element 1. Furthermore, trap layers 12 and 120 are integrally formed with each other. The other features are same as in the first embodiment.

In oxygen concentration sensor element 1 of this embodiment, it is possible to make the thickness of trap layer 120 thicker, so that the trapping performance can be improved. The other operation and effect are same as in the first embodiment.

Next, a fourth embodiment of the present invention is described.

In each of the above first to third embodiments, a cup-shaped oxygen concentration sensor element is used, however, in this embodiment, a laminated type oxygen concentration sensor element is used as shown in FIGS. 5–9.

Figure 5:
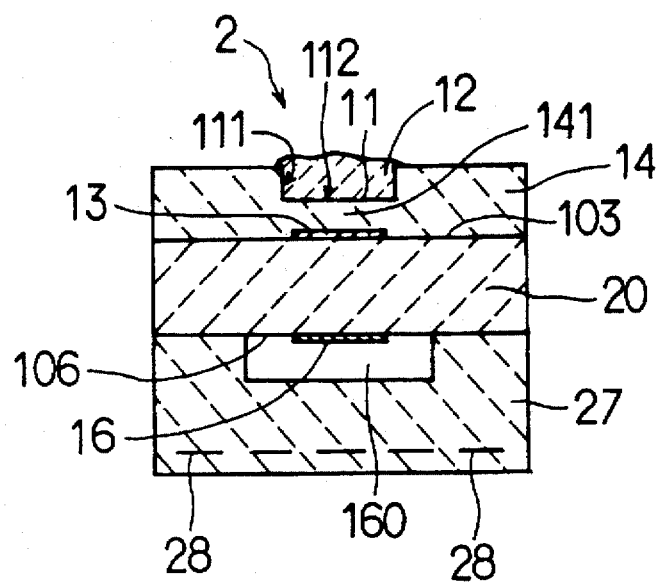
FIG. 5 is a sectional view of an oxygen concentration sensor element according to a fourth embodiment.

In FIG. 5, a laminated type oxygen concentration sensor element 2 has a alumina base 27 with a built-in heater 28. Alumina base 27 is laminated on an inner surface 106 of a plate-shaped solid electrolyte 20 to form a reference gas chamber 160 therebetween. A reference electrode 16 is disposed on a portion facing reference gas chamber 160 on inner surface 106 of solid electrolyte 20.

On the other hand, a measured gas side electrode 13 is disposed on an outer surface 103 of solid electrolyte 20. A diffusion resistance portion 14 made of a porous layer is fixed on the surface of measured gas side electrode 13.

A concave portion 11 having a trap layer 12 is disposed at a position 141 facing at least measured gas side electrode 13 of diffusion resistance portion 14.

The followings are examples of the shape of concave portion 11 and trap layer 12.

Figure 7:
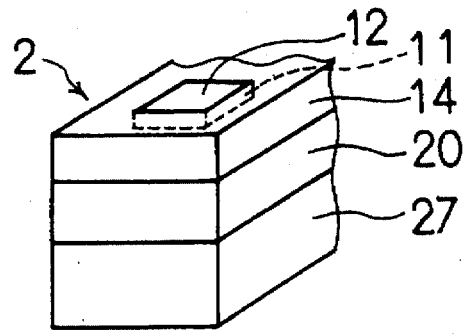
FIG. 7 is a perspective view of another oxygen concentration sensor element according to the fourth embodiment.

In FIGS. 5 and 7, the shape of concave portion 11 is a square hollow formed on the surface of diffusion resistance portion 14.

Figure 6:
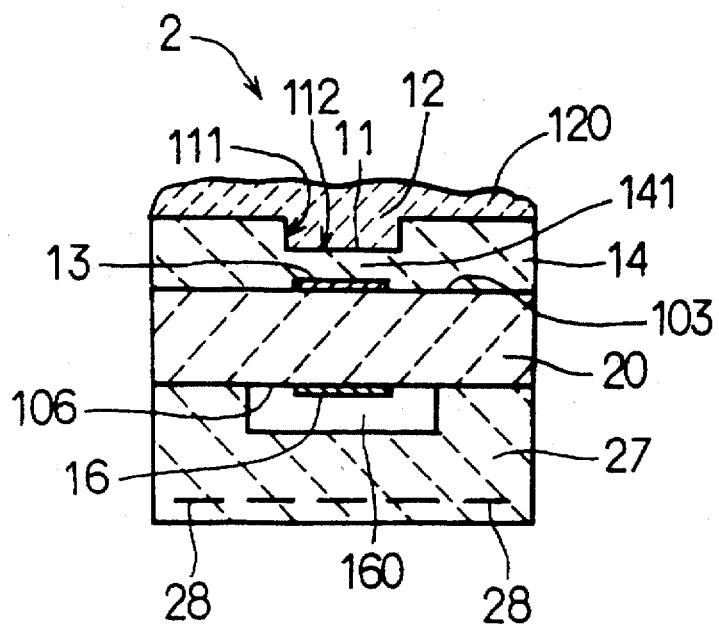
FIG. 6 is a sectional view of another oxygen concentration sensor element according to the fourth embodiment.

In FIG. 6, trap layer 12 is formed on the surface of concave portion 11 and trap layer 120 is formed on the surface of a part of diffusion resistance portion 14 other than concave portion 11 in the same manner as the third embodiment.

Figure 8:
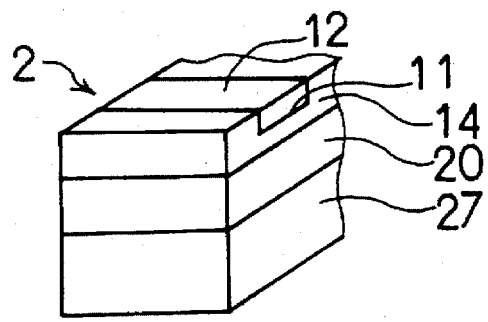
FIG. 8 is a perspective view of a further oxygen concentration sensor element according to the fourth embodiment.

In FIG. 8, a shape of concave portion 11 is like a rectangular ditch formed on the surface of diffusion resistance portion 14.

Figure 9:
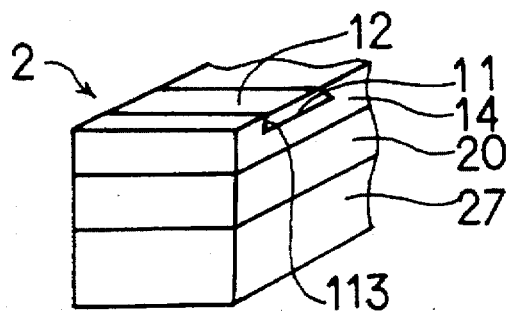
FIG. 9 is a perspective view of a still further oxygen concentration sensor element according to the fourth embodiment.

In FIG. 9, a concave portion 11 has an inclined wall surface 113 extending toward the bottom of concave portion 11 in the same manner as the second embodiment. The other features are same as in the first embodiment.

In oxygen concentration sensor element 2 of the embodiment shown in FIGS. 5 and 7, a contacting surface of concave portion 11 with trap layer 12 becomes larger, so that it is more difficult for concave portion 11 and trap layer 12 to be separated. The other operation and effect are same as in the first embodiment.

Next, a fifth embodiment of the present invention is described.

Figure 10:
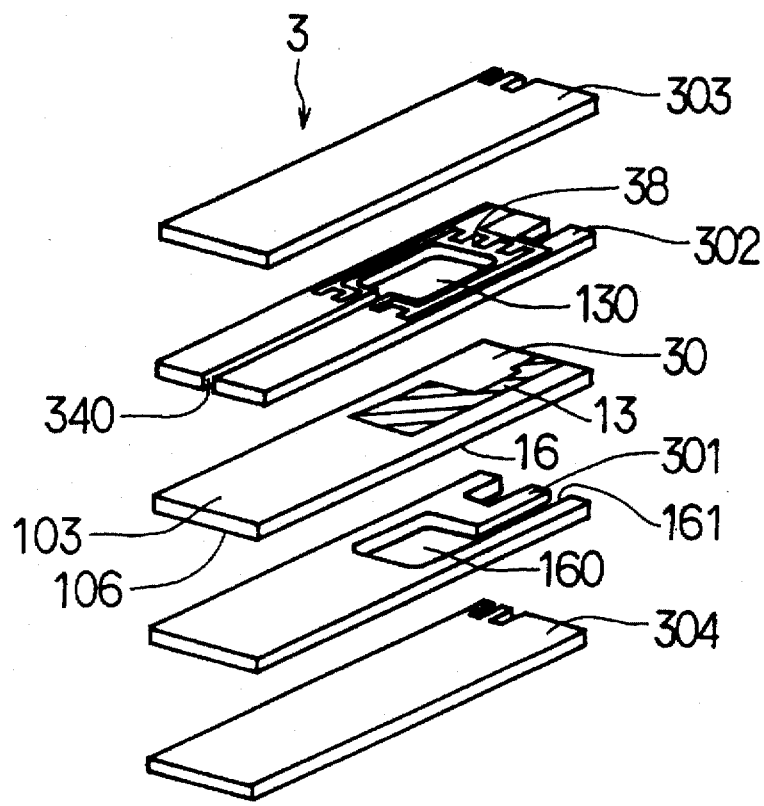
FIG. 10 is a perspective development view of an oxygen concentration sensor element according to a fifth embodiment.
Figure 11:
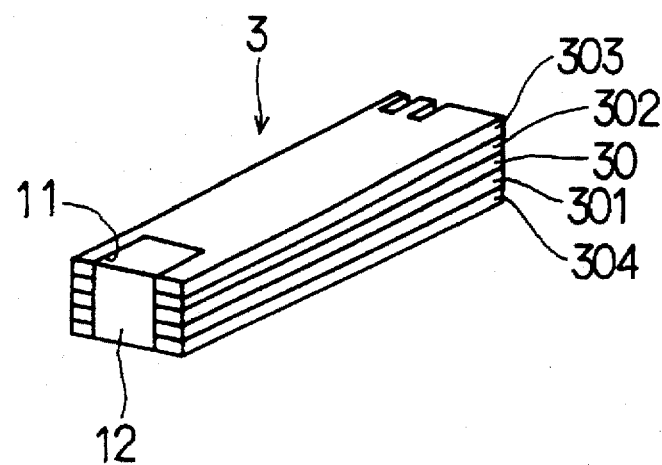
FIG. 11 is a perspective view of a modification of the fifth embodiment.

In this embodiment, as shown in FIGS. 10 and 11, diffusing hole is provided as a diffusion resistance portion in a laminated type oxygen concentration sensor element.

In FIG. 10, an oxygen concentration sensor element 3 includes four ceramic plates 301, 302, 303 and 304 and a solid electrolyte 30 having a identical shape to ceramic plates 301, 302, 303 and 304. These ceramic plates 301-304 and solid electrolyte 30 are integrally laminated.

Ceramic plate 301 has a penetrating rectangular ditch 160 and a penetrating slit-shaped ditch 161 communicating with penetrating rectangular ditch 160. A reference electrode 16 is provided on the inner surface 106 facing ditch 160 on solid electrolyte 30. A measured gas side electrode 13 is provided on an outer surface 103 facing a penetrating slit-shaped ditch 130, which will be described later.

On the other hand, a heater 38 is provided on ceramic plate 302 in a manner to surround penetrating slit-shaped ditch 130.

A penetrating slit-shaped ditch 340, which extends from penetrating slit-shaped ditch 130 to an end of ceramic plate 302, is formed on ceramic plate 302. By laminating solid electrolyte 30 and ceramic plate 303 on the both surfaces of ceramic plate 302, penetrating slit-shaped ditch 340 forms a thin rectangular hole functioning as a diffusion resistance portion.

When ceramic plates 301-304 and solid electrolyte 30 are integrally laminated, ditch 130 serves as a measured gas chamber defined by plates 302 and 303 and solid electrolyte 30, while ditch 160 serves as a reference gas chamber defined by solid electrolyte 30 and plates 301 and 304. Ditch 161 functions as an atmosphere introducing passage.

As shown in FIG. 11, concave portion 11 having trap layer 12 is provided at an end of oxygen concentration sensor element 3. The other features are same as in the first embodiment.

In this embodiment, a contacting surface of concave portion 11 with trap layer 12 becomes much larger, so that it is very difficult for both concave portion 11 and trap layer 12 to be separated. Moreover, measured gas can contact with oxygen concentration sensor element 3 in a larger three-dimensional area. The other operation and effect are same as in the first embodiment.

Figure 12:
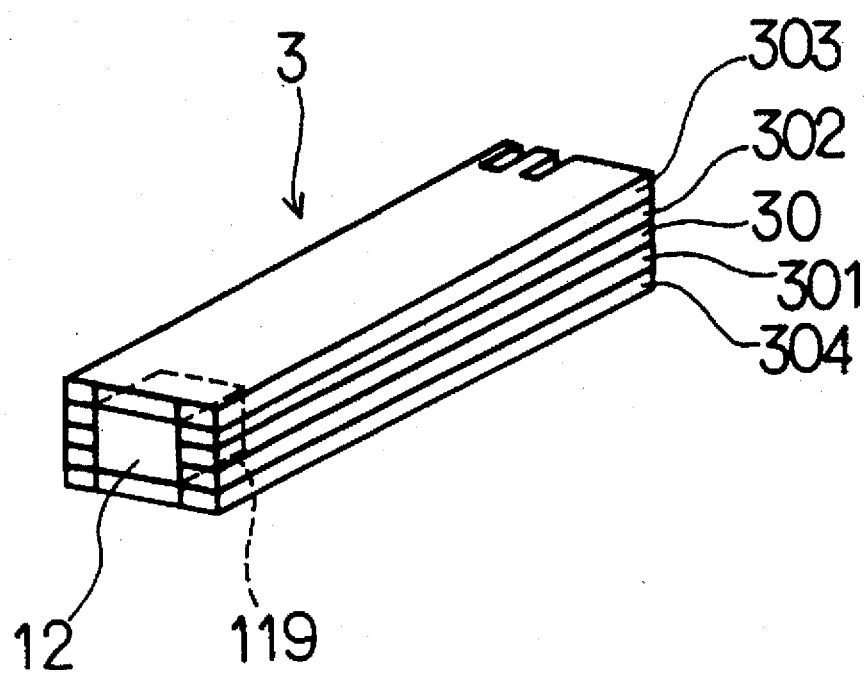
FIG. 12 is a perspective view of the oxygen concentration sensor element according to the fifth embodiment.

As shown in FIG. 12, four sides of concave portion 119 can be closed instead of concave portion 11 being a slit-like shape as shown in FIG. 11.

Next, a sixth embodiment of the present invention is described.

Figure 13:
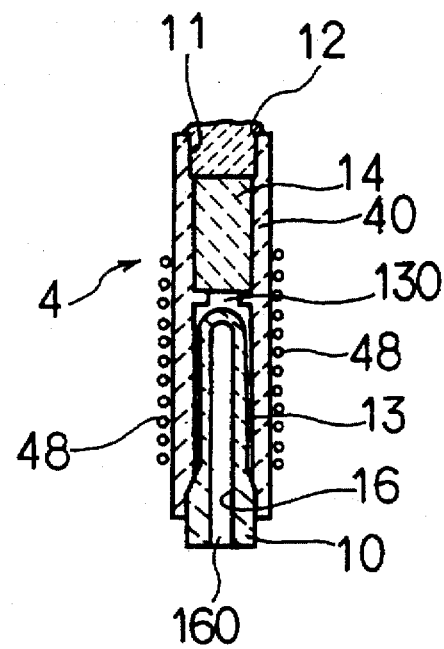
FIG. 13 is a sectional view of an oxygen concentration sensor element according to a sixth embodiment.

As shown in FIG. 13, in an oxygen concentration sensor element 4 of this embodiment, a diffusion resistance portion 14 and a solid electrolyte 10 are disposed separately in a ceramic housing 40.

Ceramic housing 40 has a measured gas chamber 130 therein. A cup-shaped solid electrolyte 10 having a reference electrode 16 and a measured gas side electrode 13 is inserted in measured gas chamber 130.

Diffusion resistance portion 14 is disposed adjacent to measured gas chamber 130 in ceramic housing 40. A concave portion 11 having a trap layer 12 is formed in diffusion resistance portion 14 made of a porous layer. A heater 48 is disposed outside ceramic housing 40.

In this embodiment, solid electrolyte 10 and diffusion resistance portion 14 are formed separately, solid electrolyte 10 will not be damaged when forming concave portion 11. The other operation and effect are same as in the first embodiment.

Next, a seventh embodiment of the present invention is described.

Figure 14:
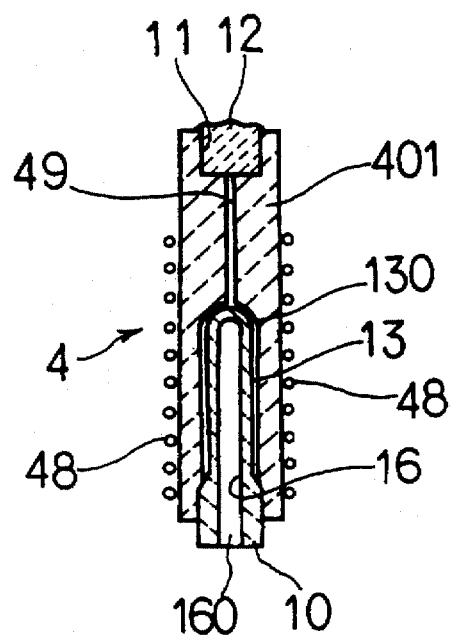
FIG. 14 is a sectional view of an oxygen concentration sensor element according to a seventh embodiment.

As shown in FIG. 14, this embodiment has a similar structure as the sixth embodiment, and includes a thin rectangular hole 49 as a diffusion resistance portion.

A ceramic housing 401 of oxygen concentration sensor element 4 has a measured gas chamber 130 and a pore 49 communicating between measured gas chamber 130 and the outside.

A concave portion 11, in which a trap layer 12 is provided, is formed at an edge where hole 49 communicates with the outside. The other operation and effect are same as in the first embodiment.

In this embodiment, solid electrolyte 10 will not be damaged in the same way as the sixth embodiment. The dimension of hole 49 can be easily confirmed. The other operation and effect are same as in the first embodiment.

Next, an eighth embodiment of the present invention is described.

Figure 15:
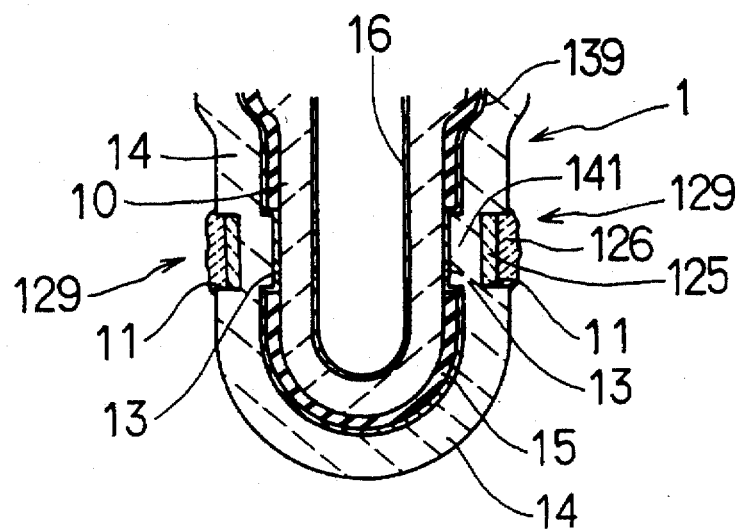
FIG. 15 is a sectional view of an oxygen concentration sensor element according to an eighth embodiment.
Figure 16:
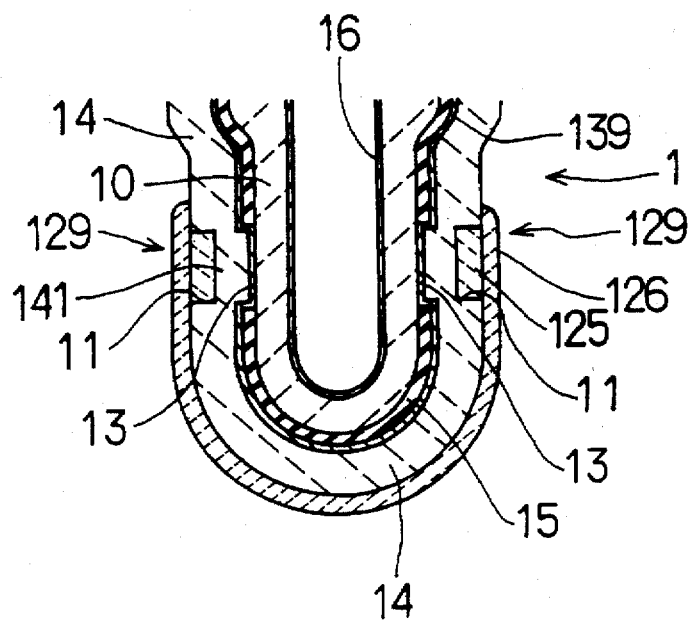
FIG. 16 is a sectional view of another oxygen concentration sensor element according to the eighth embodiment.

In this embodiment, as shown in FIGS. 15 and 16, an oxygen concentration sensor element 1 includes a cup-shaped solid electrolyte 10, and a trap layer 129 made of plural porous layers.

As shown in FIG. 15, trap layer 129 has a double-layered structure. A porous layer 126 of 40-50% porosity is formed on the surface of a porous layer 125 of 20-30% porosity. The other features are same as in the first embodiment.

As shown in FIG. 16, trap layer 129 has a double-layered structure. Porous layer 125 of 20-30% porosity is disposed in a concave portion 11. Porous layer 126 of 40-50% porosity is disposed on the surfaces of porous layer 125 and a diffusion resistance portion 14.

Since oxygen concentration sensor element 1 includes trap layer 129 having a double-layered structure, it is possible to make a trap layer much thicker compared with a trap layer having a single layer.

Further, the porosity of porous layer 126, i.e., an outer layer, is higher than that of porous layer 125, i.e., an inner layer, poison having a larger particle diameter can be trapped by porous layer 125 and poison having a smaller particle diameter can be trapped by porous layer 126.

In this way, trap layer 129 is prevented from being clogged and can trap contamination more efficiently. The other operation and effect are same as in the first embodiment.

The present invention should not be limited to the above-described embodiments but may be modified in many other ways without departing from the spirit of the invention.

What is claimed is:

1. A limiting current type oxygen concentration sensor element comprising:

a solid electrolyte;

a reference electrode formed at one side of said solid electrolyte;

a measured gas side electrode formed at the other side of said solid electrolyte;

a porous diffusion resistance portion formed on said measured gas side electrode through which measured gas passes and providing diffusion resistance thereto, said diffusion resistance portion including a concave portion formed at a position corresponding to a position of said measured gas side electrode; and a porous trap layer disposed in said concave portion for trapping contamination in measured gas, a porosity of said porous trap layer being larger than a porosity of said porous diffusion resistance portion.

2. A limiting current type oxygen concentration sensor element according to claim 1, wherein said concave portion includes a bottom surface and an inclined wall which inclines toward said bottom surface in such a manner that said bottom surface and said inclined wall forms an acute angle.

3. A limiting current type oxygen concentration sensor element according to claim 1, wherein said trap layer is formed on another portion of said diffusion resistance portion in addition to said concave portion.

4. A limiting current type oxygen concentration sensor element according to claim 1, wherein said trap layer includes a plurality of trap layers.

5. A limiting current type oxygen concentration sensor element according to claim 4, wherein each of said plurality of layers of said trap layer has different porosity with the other.

6. A limiting current type oxygen concentration sensor element according to claim 1, wherein said diffusion resistance portion is a porous layer.

7. A limiting current type oxygen concentration sensor element according to claim 1, wherein said diffusion resistance portion is a hole.

8. A method for manufacturing a limiting current type oxygen concentration sensor element including a solid electrolyte, a reference electrode formed at one side of said solid electrolyte, and a measured gas side electrode at the other side of said solid electrolyte, said method comprising steps of:

forming a diffusion resistance portion having diffusion resistance on said measured gas side electrode;

forming a concave portion on said diffusion resistance portion; and providing a trap layer for trapping concentration in a measured gas in said concave portion, wherein said step of forming a concave portion includes:

obtaining a desired thickness ($L_1$) of said diffusion resistance portion from a desired output value ($I_1$) of said oxygen concentration sensor element based on a relationship between a layer thickness ($L_0$) of an original diffusion resistance portion and a first output value ($I_0$) of said oxygen concentration sensor element; and reducing a thickness of said diffusion resistance portion to said desired thickness ($L_1$).

9. A method for manufacturing a limiting current type oxygen concentration sensor element according to claim 8, further comprising:

obtaining a thickness ($\Delta L$) to be cut of said diffusion resistance portion from said desired thickness ($L_1$) of said diffusion resistance portion, which has been obtained from a desired output value ($I_1$) of said oxygen concentration sensor element based on the relationship between said layer thickness ($L_0$) of said original diffusion resistance portion and said first output value ($I_0$) of said oxygen concentration sensor element, wherein said thickness of diffusion resistance portion is reduced by cutting with said thickness ($\Delta L$).

10. A method for manufacturing a limiting current type oxygen concentration sensor element according to claim 9, wherein said thickness ($\Delta L$) to be cut of said diffusion resistance portion is obtained by a following equation:

$$\begin{aligned}\Delta L &= L_0 - L_1 \\ &= L_0\{1 - (L_1/L_0)\} \\ &= L_0\{1 - (I_0/I_1)\}.\end{aligned}$$

11. A method for manufacturing a limiting current type oxygen concentration sensor element according to claim 8, wherein said trap layer has larger porosity than said diffusion resistance portion.

12. A method for manufacturing a limiting current type oxygen concentration sensor element including a solid electrolyte, a reference electrode formed at one side of said solid electrolyte, and a measured gas side electrode at the other side of said solid electrolyte, said method comprising:

forming a diffusion resistance portion having diffusion resistance on said measured gas side electrode;

obtaining a desired thickness ($L_1$) of said diffusion resistance portion from a desired output value ($I_1$) of said oxygen concentration sensor element based on a relationship between a layer thickness ($L_0$) of an original diffusion resistance portion and a first output value ($I_0$) of said oxygen concentration sensor element; and reducing a thickness of said diffusion resistance portion to said desired thickness ($L_1$).

13. A method for manufacturing a limiting current type oxygen concentration sensor element according to claim 12, further comprising:

obtaining a thickness ($\Delta L$) to be cut, of said diffusion resistance portion, which has been obtained from a desired output value ($I_1$) of said oxygen concentration sensor element based on the relationship between said layer thickness ($L_0$) of said original diffusion resistance portion and said first output value ($I_0$) of said oxygen concentration sensor element, wherein said thickness of diffusion resistance portion is reduced by cutting said thickness ($\Delta L$).

14. A method for manufacturing a limiting current type oxygen concentration sensor element according to claim 13, wherein said thickness ($\Delta L$) to be cut, of said diffusion resistance portion, is obtained by a following equation;

$$\begin{aligned} \Delta L &= L_0 - L_1 \\ &= L_0\{1 - (L_1/L_0)\} \\ &= L_0\{1 - (I_0/I_1)\}. \end{aligned}$$

15. A method for manufacturing a limiting current type oxygen concentration sensor element according to claim 12, wherein said thickness of said diffusion resistance portion is set to said desired thickness by forming a concave portion on a surface of said diffusion resistance portion at a position corresponding to said measured gas side electrode.

16. A method for manufacturing a limiting current type oxygen concentration sensor element according to claim 15, wherein said concave portion includes a bottom surface and an inclined wall which inclines toward said bottom surface in such a manner that said bottom surface and said inclined wall form an acute angle.

17. A method for manufacturing a limiting current type oxygen concentration sensor element according to claim 15, wherein a porous trap layer is formed at least in said concave portion.

18. A method for manufacturing a limiting current type oxygen concentration sensor element according to claim 17, wherein said trap layer includes a plurality of layers.

19. A method for manufacturing a limiting current type oxygen concentration sensor element according to claim 17, wherein said trap layer has a larger porosity than said diffusion resistance portion.

* * * * *